United States Patent [19]

Salyer

[11] 4,265,257

[45] May 5, 1981

[54] POWER DRIVEN DENTAL FLOSS CLEANER

[76] Inventor: James R. Salyer, 816 Bacon Ave., Dover, Del. 19901

[21] Appl. No.: 58,381

[22] Filed: Jul. 17, 1979

[51] Int. Cl.³ .............................................. A61C 15/00
[52] U.S. Cl. .................................................. 132/92 R
[58] Field of Search ...................... 132/91, 92 R, 92 A, 132/93, 89, 90

[56] References Cited

U.S. PATENT DOCUMENTS

| | | | |
|---|---|---|---|
| 2,376,750 | 5/1945 | Bell | 132/92 R |
| 2,381,530 | 8/1945 | Dembenski | 132/92 A |
| 3,421,524 | 1/1969 | Waters | 132/92 R |
| 3,759,274 | 9/1973 | Warner | 132/92 R |

Primary Examiner—Robert A. Hafer
Attorney, Agent, or Firm—Sixbey, Friedman & Leedom

[57] ABSTRACT

A power driven dental floss holder for cleaning the teeth with dental floss is provided. The power driven dental floss holder comprises a power unit 14 on which is mounted an elongated vibratory arm 12 and an elongated nonvibratory arm 22 having dental floss 21 threaded in a triangular configuration between the distal ends thereof. The novel dental floss holder may be easily and quickly moved between the teeth to control the degree of vibratory motion imparted to the floss and therefore to tooth surfaces, thus minimizing the likelihood of injury to gum tissues.

31 Claims, 11 Drawing Figures

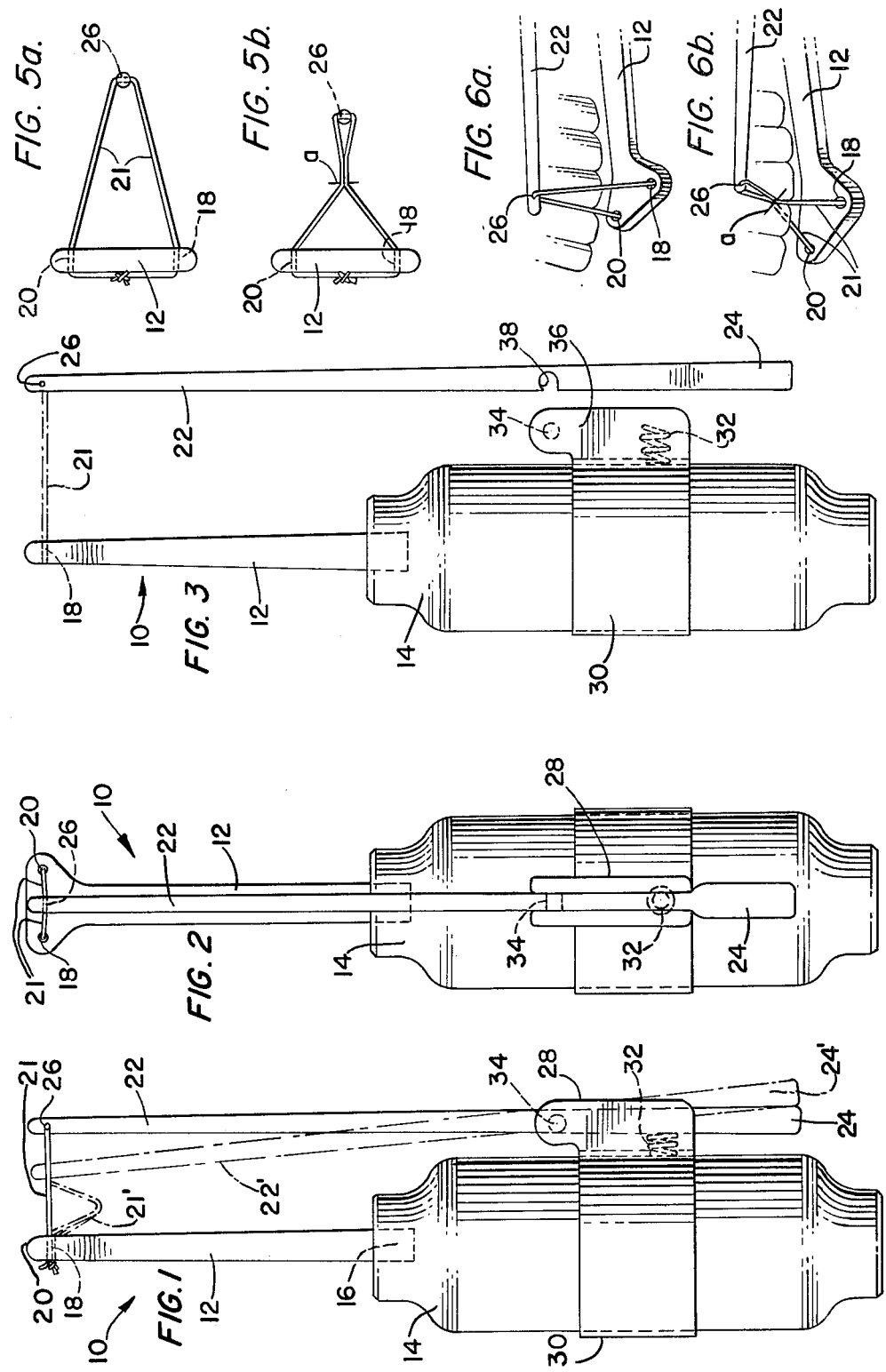

POWER DRIVEN DENTAL FLOSS CLEANER

DESCRIPTION

1. Technical Background

The present invention relates to apparatus for cleaning the teeth and, specifically, to a power driven holder for dental floss which provides an efficient, effective means for cleaning tooth surfaces.

2. Background Art

The dental profession has long advocated cleaning with dental floss as an essential part of daily dental hygiene. It is widely recognized that the proper use of dental floss is an effective means for preventing both tooth decay and gum disease. An ideal holder for dental floss is one which enables the user to maneuver the holder so that floss may be inserted easily between the teeth, especially between the molars at the back of the mouth. In addition, a power driven floss holder should permit the user to exercise the maximum control possible over the tension of the floss and should avoid a sawing, back-and-forth motion of the floss which is likely to cause injury to gum tissue.

Perhaps the most widely known method of cleaning the teeth with dental floss is to hold a length of floss between the thumb and forefinger of each hand. The floss is stretched taut, inserted between two teeth and then moved up and down or back and forth with a sawing motion to effect the desired cleaning. Such a method may be effective in removing food or other particles trapped between the teeth and in cleaning tooth surfaces, but the sawing motion is very likely to cause injury by cutting tender gum tissue. Moreover, although it is not difficult to control floss tension during a manual flossing operation, since the tightly stretched floss can be readily released, it can be very difficult to maneuver the dental floss as it is held by both hands to clean properly between the molars.

Holders for dental floss have been proposed in an attempt to alleviate the problems involved in first inserting dental floss held by the thumb and forefinger of both hands between the teeth and then properly maneuvering the hand held floss to achieve the desired cleaning. In fact, dental floss holders such as those disclosed in U.S. Pat. Nos. 1,479,364 and 1,780,045 have enhanced somewhat the maneuverability of the floss during cleaning. Unfortunately, however, these dental floss holders provide little or no control over the tension of the floss during normal flossing operations so that the tightly stretched floss cannot be readily released. Moreover, such prior art dental floss holders clean by using the same back and forth, sawing motion employed during a manual flossing operation. This motion can irritate and injure tender gum tissue, and the discomfort which may result from flossing with a sawing motion can discourage persons from following their dentists' orders to floss frequently.

It has also been proposed to attach a dental floss holder to a power driven vibrating unit, such as those conventionally used to drive an electric toothbrush. The power driven unit imparts a vibratory motion to the dental floss holder which enhances the cleaning action of the floss. While a powered flossing unit, such as is disclosed in U.S. Pat. Nos. 3,421,524 and 3,534,745, provides a better cleaning action and is more convenient to use and thus encourages more frequent flossing, such units have not entirely overcome the problems associated with maneuverability of the floss and irritation of gum tissue. The combination of the vibrating floss holder and the power unit tends to be bulky and can be almost as awkward to maneuver between the molars as hand held floss. Moreover, no means for controlling floss tension is provided so that the floss remains stretched taut in the holder at all times. The operation of the power unit causes the floss holder to vibrate and imparts a sawing motion to the tightly stretched floss which continues until the power unit is turned off. This motion is highly effective in cleaning tooth surfaces. However, if the moving floss comes in contact with gum tissue, the strong sawing motion imparted to it by the power driven vibrating unit will readily cut the tender gum tissue, thus causing the user considerable discomfort. Since there is no way to control floss tension on such a unit, the only way in which the user may obtain relief when the floss begins to cut his gums is to move the tightly stretched floss strand away from his gums and turn off the power unit. Neither of these operations is performed quickly or easily if the user has injured his gums while flossing with a power driven flosser. In addition, inserting and then removing the prior art power flossers must be carried out with extreme care to avoid striking the teeth with the vibrating portion of the unit. Even when these power flossers are maneuvered carefully, it is difficult to keep the two floss holding arms from hitting the teeth since the arms are quite close together and both vibrate simultaneously.

DISCLOSURE OF THE INVENTION

A primary object of the present invention is to provide a novel power driven dental floss holder which includes a fixed, vibratory arm and a removable pivoted arm for holding and controlling the tension of dental floss threaded therebetween.

An additional object of the present invention is to provide a power driven dental floss holder which maintains the floss in a triangular configuration between a fixed, vibratory arm and a removable pivotal arm which prevents the vibrating portion of the floss holder from striking the teeth and which concentrates any sawing movement imparted to the floss in the section of the floss farthest away from teeth and gums.

Still another object of the present invention is to provide a power driven dental floss holder which includes means for quickly adjusting the floss tension from taut to slack, thereby avoiding injury to tender gum tissue.

Yet another object of the present invention is to provide a power driven dental floss holder including a removable arm which may be separated from the power unit and easily maneuvered by hand to clean the teeth in all parts of the mouth.

A further object of the present invention is to provide a power driven dental floss holder which cleans the teeth efficiently and effectively with a vibrating motion which is gentle and non-traumatic to the gums.

Further objects and advantages of the invention will become apparent from the following description and claims and from the accompanying drawings.

In accordance with the present invention a holder for dental floss is provided comprising a vibratory power unit which supports an elongated vibratory arm and an elongated nonvibratory arm which is preferably pivotally attached to and removable from the power unit and includes a spool of dental floss. The vibratory arm includes a wide distal end having two opposed spaced means for receiving a strand of dental floss which is threaded through a single floss receiving means in the distal end of the nonvibratory arm so that the floss is maintained in a triangular configuration.

BRIEF DESCRIPTION OF THE DRAWINGS

FIG. 1 is a side view of the dental floss holder of the present invention showing the nonvibratory arm in two positions;

FIG. 2 is a plan view of the dental floss holder of FIG. 1;

FIG. 3 is a side view of the dental floss holder of FIG. 1 showing the removable nonvibratory arm detached from its clamp;

FIG. 4 is a perspective view of the dental floss holder of FIG. 1 showing the detail of the clamp for holding the removable nonvibratory arm;

FIGS. 5a and 5b are plan views showing the distal portion of the two arms of the floss holder of FIG. 1 holding the floss and illustrating the configurations of the floss before and after insertion between the teeth;

FIGS. 6a and 6b are diagrammatic views illustrating the placement of the floss as it is held by the floss holder between the teeth;

FIG. 7 is a view of the distal portion of a second embodiment of the floss holder of the present invention;

FIG. 8 is an exploded view of another embodiment of the removable nonvibratory arm of the present invention; and FIG. 9 is an enlarged view of the distal end of the nonvibratory arm of the embodiment shown in FIG. 8 showing a floss cutting edge.

BEST MODE FOR CARRYING OUT THE INVENTION

Referring to the drawings, the dental floss holder of the present invention is illustrated in FIG. 1. The floss holder, generally indicated at 10, includes an elongated arm 12 which is designed to cooperate with a vibratory power unit 14. The power unit 14 may be the type used to drive a conventional electric toothbrush, although any similar vibratory power unit will suffice. In either case, the proximal end 16 of arm 12 is formed to fit into and may be removable from power unit 14. The distal end of arm 12 is wide and has opposed spaced means 18 and 20 to receive strands 21 of dental floss. Opposed spaced means 18 and 20 can be holes, slots or the like.

A second nonvibratory elongated arm 22 is mounted, preferably pivotally, on power unit 14 so as not to be driven thereby. Second arm 22 includes a handle 24 at its proximal end. The distal end of arm 22 includes means 26 for receiving a strand of dental floss 21. Arm 22 may also include means (not shown in FIG. 1) for readily engaging and disengaging clamp 28 by which arm 22 is mounted on power unit 14.

Clamp 28 which engages arm 22 may be attached to power unit 14 by any convenient means, such as by strap 30 formed integrally with clamp 28 and fitted tightly about the circumference of power unit 14 as shown in FIG. 1. Clamp 28, which is discussed in further detail hereinbelow, includes a spring element 32 biased outwardly from power unit 14. This spring element may be a coil spring as shown; however, it is contemplated that any comparable spring element may be employed.

FIG. 1 illustrates the manner in which the tension of floss 21 is varied when arm 22 is pivotally engaged in clamp 28. The solid lines depict the position of arm 22 when floss 21 is stretched tight between arm 12 and arm 22. Viewed from above, as will be discussed later, taut floss strand 21 forms a triangle with the apex at floss receiving means 26 and the base between floss receiving means 18 and 20. To place arm 22 in this position, it is necessary to apply and maintain pressure on handle 24 such as would be applied by the thumb if power unit 14 is held in the hand. The pressure on arm 22 compresses spring element 32 and positions arm 22 substantially parallel to arm 12, stretching floss 21 tightly between the distal ends of arm 22 and arm 12. To release the floss tension, it is necessary only to release the pressure on handle 24 by lifting the thumb. Spring element 32 immediately pushes arm 22 outwardly from power unit 14 to the position designated by dashed lines 22' and causes the floss to hang slack as depicted by 21'. To tighten the floss, pressure is applied at 24' to compress spring element 32 and pivot arm 22' to the position occupied by arm 22.

Although arm 22 of the floss holder of the present invention may be rigidly mounted to power unit 14, it is preferred to utilize a pivotal mounting. A pivotal mounting allows the position of arm 22 relative to arm 12 to be changed easily which provides more control over the tension of the dental floss than if arm 22 is not pivotally mounted. Utilization of a fulcrum 34 about which arm 22 may be moved accomplishes this result.

It is additionally preferable to provide means for making arm 22 removable from clamp 28 on power unit 14. Removing arm 22 from clamp 28 enhances the maneuverability of the floss holder, since elongated arm 22 occupies much less space than the entire floss holder. Once arm 22 is free from the rest of the holder, it may be guided with one hand to insert floss between two teeth that are generally hard to reach, such as the back molars, while power unit 14 is held in the other hand. To floss teeth that are closer to the front of the mouth, arm 22 is re-engaged in clamp 28, and the entire floss holder may be manipulated with one hand. When disengaged from clamp 28, arm 22 may be moved at any angle and in any direction relative to arm 12, permitting the user not only great maneuverability but also control over floss tension, since to change the floss tension the user has only to move the distal end of arm 22 toward or away from the distal end of arm 12.

Any one of a number of well known means could be utilized to mount arm 22 to power unit 14 and to provide the pivoting movement necessary to adjust floss tension between arms 12 and 22 while allowing easy disengagement and re-engagement of arm 12. One arrangement which fulfills all the necessary functions is illustrated in FIGS. 3 and 4. Here clamp 28 is provided with a fulcrum 34 which allows the distal end of arm 22 to move toward and away from the distal end of arm 12 to control the tension of floss 21. In order for this movement to be possible, fulcrum 34 of clamp 28 must be far enough from power unit 14 so that arm 22 is substantially parallel to arm 12 when the floss strand between them is stretched taut. This is accomplished by providing opposed parallel projections 36 which extend outwardly from power unit 14 to form the sides of clamp 28 as shown in FIG. 2. Fulcrum 34 bridges projections 36 at a distance from power unit 14 which positions arm 22 parallel to arm 12 and still allows sufficient pivitol movement of arm 22 to vary floss tension from taut to slack. To provide easy disengagement and re-engagement of arm 22 from clamp 28 and still provide the desired pivotal movement, arm 22 includes a socket 38 which is shaped to fit around fulcrum 34. The design of socket 38 should permit arm 22 first to snap onto fulcrum 34 easily and to remain securely retained on fulcrum 34 while arm 22 is pivotally moved and to adjust floss tension and then to be removed without difficulty. The ready removal and reattachment of arm 22 provided by socket 38 allows the user substantially more control over both the insertion of the floss between the teeth and the tension at which flossing occurs than heretofore possible. Because the user has a large amount of control over the floss, flossing can be carried out efficiently with maximum safeguard against injury to the gums.

FIGS. 5a and 5b and FIGS. 6a and 6b illustrate in greater detail the advantages presented by the triangular floss configuration. FIGS. 5a and 5b show the distal ends of arms 12 and 22 viewed from above, and FIGS. 6a and 6b show the placement between the teeth of dental floss 21 which has been stretched tight between arms 12 and 22. As previously described, floss 21 is threaded through floss receiving means 18 and 20 in the wide distal end of arm 12 and through floss receiving means 26 in the distal end of arm 22 to form a triangle having two equal sides, the base of which is the section of floss between floss receiving means 18 and 20 and the apex of which is at floss receiving means 26. A strand of dental floss is threaded as described and the two ends knotted securely together, preferably at a point between floss receiving means 18 and 20 so that the knot does not interfere with the cleaning action provided by the floss. Alternatively, the free ends of the floss may be secured to the arm 22 after the floss has been threaded through the floss receiving means 18 and 20. For example, one free end might be inserted through the floss receiving means 26 and then tied to the remaining free end, or a suitable clamp may be provided to secure the free ends of the floss to the arm 22.

FIG. 7 illustrates an arrangement for securing the free ends of the floss to the arm 22. In this embodiment, the floss is looped through slots 18a and 20a in the arm 12 and the free ends of the floss are clamped to the arm 22 by a sliding ring 40. The outer end of the arm 22 may be flared outwardly at 42 so that the ring 40 may slide to clamp the floss ends against this flared portion.

FIG. 8 illustrates a further embodiment of the nonvibratory arm of the present invention. In this embodiment, nonvibratory arm 48 has been widened in the middle portion to hold a spool of dental floss 50 which may be readily replaced as needed. To accomplish this, arm 48 is divided into three sections: the handle section 52, the floss containing section 54 and the distal section 56. The top of handle section 52 is threaded at 58 to receive mating threads 60 in the bottom of floss containing section 54. Floss containing section 54 is likewise threaded at 62 to receive threads 64 in the bottom of distal section 56. Threaded portions 62 and 64 of floss containing section 54 and distal section 56 may be suitably notched or drilled to allow a length of floss 66 to be easily pulled from the spool and then secured.

FIG. 9 illustrates an enlarged view of the distal end of nonvibratory arm 22 with sliding ring 40, as shown in FIG. 7. Sliding ring 40 may provide, as shown in FIG. 9, a notched cutting edge for the convenience of the user. The proximal end of ring 40 includes a sharpened inner edge 44 and notch 46 through which the floss may be drawn and cut.

Although ring 40 has been shown to secure the dental floss by sliding along nonvibratory arm 22, it is contemplated that it could also secure the floss in other ways, such as by providing mated threads in ring 40 and nonvibratory arm 22 whereby ring 40 would screw onto arm 22.

The triangular floss configuration assures that any back and forth or sawing motion imparted by vibratory arm 12 will be confined to that portion of the floss between floss receiving means 18 and 20 on arm 12. This remains the case despite the changes which occur in the angle at which arm 22 is held in relation to vibratory arm 12. In addition, maintaining the floss in a triangular configuration as described prevents vibratory arm 12 from striking the teeth.

During a flossing operation with the novel holder of the present invention, floss strands 21 are inserted between the teeth at a point close to arm 22, as shown in FIG. 6a, and moved toward arm 12, with the result that when the teeth are at point a, as shown in FIGS. 5b and 6b, floss 21 forms two parallel strands that are so close together they appear to be a single strand between point a and arm 22. The floss between point a and arm 12 retains its triangular configuration. Since all motion imparted to the floss comes from vibratory arm 12 and none from arm 22, the vibratory motion of floss strand 21 increases along the length of the floss strand from arm 22 to arm 12. The closer the floss between the teeth is brought to arm 22, the more gentle is the motion of the floss. As the floss is moved so that the teeth are closer to arm 12, the vibratory motion increases, which enhances the cleaning action of the floss against tooth surfaces. In addition, the closer the teeth are to arm 12, the wider the separation between floss strands 21, which results in floss strands 21 contacting the surfaces of two teeth at the same time. Although this has the potential for increasing cleaning efficiency, there is also a possibility that the floss with its increased vibratory motion may cause some discomfort to already injured gums. If this occurs, the holder may be easily and quickly moved so that the floss moves back toward arm 22 to decrease the motion of the floss. Since the section of floss 21 near arm 22 moves very little, any discomfort is readily avoided, and the intensity of floss motion is easily adjusted. The triangular floss configuration not only facilitates the user's control over floss tension and avoids motions injurious to the gums, it also assures that vibratory arm 12 will never hit the teeth. When floss strands 21 are inserted between the teeth close to arm 22 and then moved toward arm 12, as shown in FIGS. 6a and 6b, a point along the floss is reached beyond which the two strands which form the sides of the triangle will no longer fit between the teeth. Consequently, when this point has been reached, the flosser cannot be maneuvered to move vibratory arm 12 any closer to the teeth. Flossing operations are thus carried out at a distance along floss strands 21 away from vibratory arm 12 so that vibratory arm 12 will not contact tooth surfaces during flossing avoiding the possibility of injury to such surfaces.

The arrangement of the vibratory arm 12, floss 21 and arm 22 just described allows the user great control over the flossing operation, thus assuring that the beneficial cleaning and gum massaging action provided by employing a vibratory power unit will be maximized and that discomfort and injury to gum tissue will be eliminated or minimized. This also has the effect of encouraging frequent flossing. Moreover, the degree of control the use has over floss tension, resulting in ready avoidance of discomfort and injury to the gums, permits the floss holder of the present invention to be used comfortably and effectively by even those with tender gum tissue.

Other variations of the novel dental floss holder are contemplated to be within the scope of the present invention. By way of example, it is contemplated that the dental floss holder of the present invention could be permanently mounted on a power unit such as power unit 14 or could be a removable unit suitable for temporary attachment to the power unit of a conventional electric toothbrush or to the kind of power unit conventionally used in dental clinics and offices to power brushes, drills and the like. Moreover, it is contemplated that the triangular floss configuration of the present invention could be provided in a floss holder with a stationary arm and a removable pivotal arm which is not power driven.

Other aspects, objects and advantages of this invention can be obtained from a study of the drawings, the disclosure and the appended claims.

I claim:

1. A power driven floss holder and cleaner comprising vibratory source means, an elongated vibratory arm mounted on said vibratory source means and having a distal end spaced outwardly from said vibrating source means, said vibratory source means being operative to impart vibratory motion to said vibratory arm, and an elongated nonvibratory arm mounted upon said vibratory source means to extend in spaced relationship to said vibratory arm from substantially the distal end thereof to said vibratory source means.

2. A power driven dental floss holder as described in claim 1, wherein said vibratory source means is the power driven vibratory unit of a conventional electric toothbrush.

3. A power driven dental floss holder as described in claim 1, wherein said vibratory arm comprises an elongated shaft, the distal end of said elongated shaft being substantially wider than the proximal end.

4. A power driven dental floss holder as described in claim 3, wherein said distal end of said elongated shaft includes a pair of opposed spaced means for receiving dental floss.

5. A power driven dental floss holder as described in claim 4, wherein said dental floss receiving means comprises a pair of eyelets.

6. A power driven dental floss holder as described in claim 4, wherein said dental floss receiving means comprises a pair of slots.

7. A power driven dental floss holder as described in claim 2, wherein the proximal end of said vibratory arm is fitted to said power driven vibratory unit of a conventional toothbrush.

8. A power driven dental floss holder as described in claim 1, wherein said nonvibratory arm comprises an elongated shaft including dental floss receiving means at the distal end of said elongated shaft.

9. A power driven dental floss holder as described in claim 8, wherein said dental floss receiving means is formed by a single eyelet.

10. A power driven dental floss holder as described in claim 8, wherein said dental floss receiving means includes clamping means to clamp the ends of a strand of dental floss.

11. A power driven dental floss holder as described in claim 1, including mounting means to pivotally mount said nonvibratory arm on said power driven vibratory unit.

12. A power driven dental floss holder as described in claim 1, wherein mounting means are provided to removably mount said nonvibratory arm on said vibratory power unit.

13. A power driven dental floss holder as described in claim 1, wherein mounting means are provided to pivotally and removably mount said nonvibratory arm on said vibratory power unit.

14. A power driven dental floss holder as described in claim 13, wherein said mounting means includes clamp means for holding said nonvibratory arm and strap means for securing said clamp means to said power unit.

15. A power driven dental floss holder comprising vibratory source means, a vibratory arm mounted on said vibratory source means, said vibratory source means being operative to impart motion to said vibratory arm, and a nonvibratory arm mounted on said vibratory source means in spaced relation to said vibratory arm wherein mounting means are provided to pivotally and removably mount said nonvibratory arm on said vibratory power unit, and said mounting means includes clamp means for holding said nonvibratory arm and strap means for securing said clamp means to said power unit, wherein said clamp means includes a pair of opposed parallel sides with fulcrum means extending therebetween for imparting pivotal movement to said nonvibratory arm.

16. A power driven dental floss holder comprising vibratory source means, a vibratory arm mounted on said vibratory source means, said vibratory source means being operative to impart motion to said vibratory arm, and a nonvibratory arm mounted on said vibratory source means in spaced relation to said vibratory arm wherein mounting means are provided to pivotally and removably mount said nonvibratory arm on said vibratory power unit, said mounting means including clamp means for holding said nonvibratory arm and strap means for securing said clamp means to said power unit, wherein said clamp means includes a pair of opposed parallel sides with fulcrum means extending therebetween for imparting pivotal movement to said nonvibratory arm, and said nonvibratory arm includes socket means for removably engaging said fulcrum means.

17. A power driven dental floss holder comprising vibratory source means, a vibratory arm mounted on said vibratory source means, said vibratory source means being operative to impart motion to said vibratory arm, and a nonvibratory arm mounted on said vibratory source means in spaced relation to said vibratory arm wherein mounting means are provided to pivotally and removably mount said nonvibratory arm on said vibratory power unit, said mounting means including clamp means for holding said nonvibratory arm and strap means for securing said clamp means to said power unit, wherein said mounting means includes spring means for biasing the proximal end of said nonvibratory outwardly from said power unit, said clamp means includes a pair of opposed parallel sides with fulcrum means extending therebetween for imparting pivotal movement to said nonvibratory arm, and said nonvibratory arm includes socket means for removably engaging said fulcrum means.

18. A power driven dental floss holder as described in claim 4 or 8, wherein dental floss is threaded through said dental floss receiving means to form a triangle with the base of said triangle between said floss receiving means on said widened distal end of said vibratory arm and the apex of said triangle at said floss receiving means in said distal end of said nonvibratory arm.

19. A dental floss holder for use with the power driven vibratory unit of an electric toothbrush comprising a first elongated arm having coupling means at one end thereof for securing said first arm to said power driven vibratory unit to be driven thereby, and said first arm having a distal end spaced from said vibratory unit, a second elongated arm and mounting means to mount a second elongated arm on said power driven vibratory unit in non-driving relationship therewith, said mounting means operating to mount said second elongated arm in spaced relationship to said first elongated arm from substantially the distal end of said first elongated arm thereof to said power driven vibratory unit.

20. A dental floss holder as described in claim 19, wherein said mounting means includes clamp means to removably mount said second elongated arm on said mounting means.

21. A dental floss holder as described in claim 20, wherein said clamp means pivotally mounts said second elongated arm for pivotal movement relative to said mounting means.

22. A dental floss holder as described in claim 19, wherein said mounting means mounts said second elongated arm for pivotal movement.

23. A dental floss holder as described in claim 1, wherein said nonvibratory arm includes means for holding a supply of dental floss.

24. A dental floss holder as described in claim 23, wherein said nonvibratory arm includes a sectioned handle having at least two sections and said dental floss holding means is contained within one of said sections.

25. A dental floss holder as described in claim 19, wherein said second elongated arm includes means for holding a supply of dental floss.

26. A dental floss holder comprising a first elongated arm, a second elongated arm, and mounting means for said arms, said mounting means operating to pivotally and removably mount said second elongated arm in spaced relationship to said first elongated arm, said first and second elongated arms including at the distal ends thereof means for maintaining a strand of dental floss extending between said distal ends in a triangular configuration.

27. A dental floss holder as described in claim 26, wherein the distal end of said first elongated arm is substantially wider than the proximal end thereof, said distal end further including opposed spaced means for receiving dental floss, the distal end of said second elongated arm includes dental floss receiving means, and dental floss is threaded through said dental floss receiving means and said opposed spaced means to form a triangle with the base of said triangle extending between said opposed spaced means on said widened distal end of said first elongated arm and the apex of said triangle being positioned at said floss receiving means in the distal end of said second elongated arm.

28. A dental floss holder as described in claim 26, wherein said second elongated arm includes means for holding a supply of dental floss.

29. A dental floss holder as described in claim 23, wherein said nonvibratory arm includes cutting means to cut off said dental floss to a desired length.

30. A dental floss holder as described in claim 25, wherein said second elongated arm includes cutting means to cut off said dental floss to a desired length.

31. A dental floss holder as described in claim 26, wherein said second elongated arm includes cutting means to cut off said dental floss to a desired length.

* * * * *